(12) United States Patent
Zeller et al.

(10) Patent No.: US 11,779,279 B2
(45) Date of Patent: Oct. 10, 2023

(54) METHOD FOR POSITIONING A PATIENT COUCH IN A PATIENT RECEIVING AREA OF A MAGNETIC RESONANCE DEVICE FOR A MAGNETIC RESONANCE EXAMINATION

(71) Applicant: Siemens Healthcare GmbH, Erlangen (DE)

(72) Inventors: Mario Zeller, Erlangen (DE); Dominik Paul, Bubenreuth (DE)

(73) Assignee: Siemens Healthcare GmbH, Erlangen (DE)

(*) Notice: Subject to any disclaimer, the term of this patent is extended or adjusted under 35 U.S.C. 154(b) by 268 days.

(21) Appl. No.: 17/003,200

(22) Filed: Aug. 26, 2020

(65) Prior Publication Data

US 2021/0059558 A1    Mar. 4, 2021

(30) Foreign Application Priority Data

Aug. 27, 2019 (DE) .......................... 102019212863.7

(51) Int. Cl.
  *A61B 5/055* (2006.01)
  *G01R 33/567* (2006.01)
  *A61B 5/00* (2006.01)

(52) U.S. Cl.
  CPC .......... *A61B 5/055* (2013.01); *G01R 33/5673* (2013.01); *A61B 5/704* (2013.01)

(58) Field of Classification Search
  CPC ..... A61B 5/055; A61B 5/0077; A61B 5/0816; A61B 5/7264; A61B 5/7267; A61B 5/704;

(Continued)

(56) References Cited

U.S. PATENT DOCUMENTS 7,180,294 B2   2/2007 Kohlmuller
8,042,209 B2*  10/2011 D'Souza .............. A61N 5/1049
                                                    5/610

(Continued)

FOREIGN PATENT DOCUMENTS

DE   202016005585 U1   10/2016
DE   102015209237 A1   11/2016

OTHER PUBLICATIONS

Zeller et al; Utilizing RFID-tags for planning a magnetic resonance examination; Mar. 30, 2015.

(Continued)

*Primary Examiner* — Amelie R Davis
(74) *Attorney, Agent, or Firm* — Banner & Witcoff Ltd.

(57) ABSTRACT

Techniques are disclosed for positioning a patient couch in a patient receiving area of a magnetic resonance device for a magnetic resonance examination, which includes starting an introduction of the patient couch into the patient receiving area, acquiring monitoring data within an acquisition area of at least one sensor unit by means of the at least one sensor unit during the introduction of the patient couch into the patient receiving area, evaluating the monitoring data with respect to a selected area of an examination object and/or a selected area of the patient couch, and positioning the patient couch within the patient receiving area in dependence on an acquisition of the selected area of the examination object and/or the selected area of the patient couch in the monitoring data.

18 Claims, 2 Drawing Sheets

Figure 1:
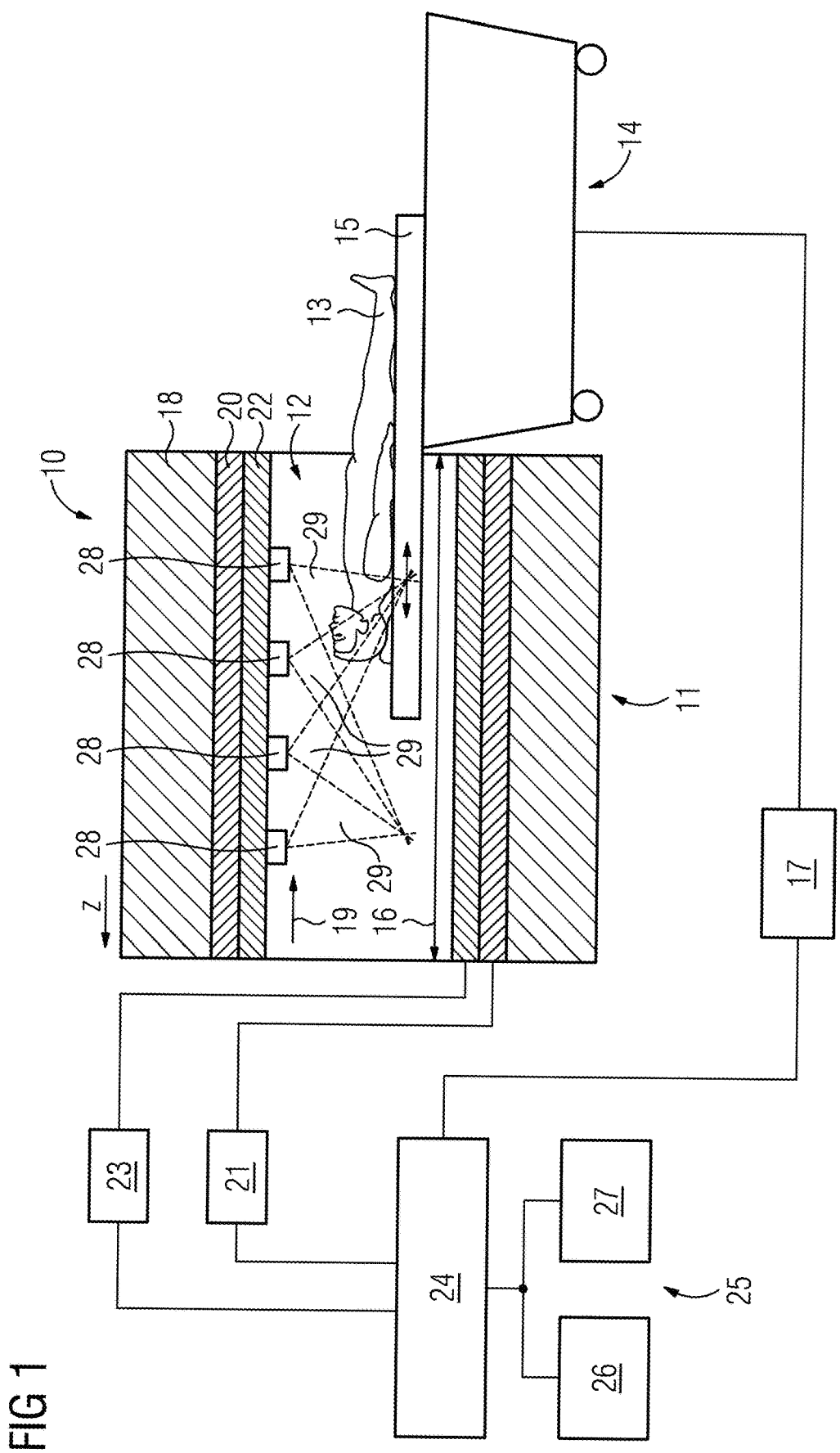

(58) Field of Classification Search
CPC ....... A61B 6/0407; A61B 6/0487; A61B 6/04; G01R 33/5673; G01R 33/543; G01R 33/283; G01R 33/5608
See application file for complete search history.

(56) References Cited

U.S. PATENT DOCUMENTS

| | | | |
|---|---|---|---|
| 9,766,308 B2* | 9/2017 | Biber | G01R 33/56509 |
| 2014/0070807 A1* | 3/2014 | Biber | G01R 33/30 324/309 |
| 2016/0338614 A1 | 11/2016 | Gall et al. | |
| 2017/0168124 A1* | 6/2017 | Ueda | A61B 5/742 |
| 2018/0070853 A1* | 3/2018 | Ehrl | G01R 33/543 |
| 2019/0175122 A1* | 6/2019 | Stahl | A61B 6/0492 |
| 2020/0054240 A1* | 2/2020 | Roland | G01R 33/543 |

OTHER PUBLICATIONS

German action dated May 25, 2020, for Application No. 10 2019 212 863.7.

* cited by examiner

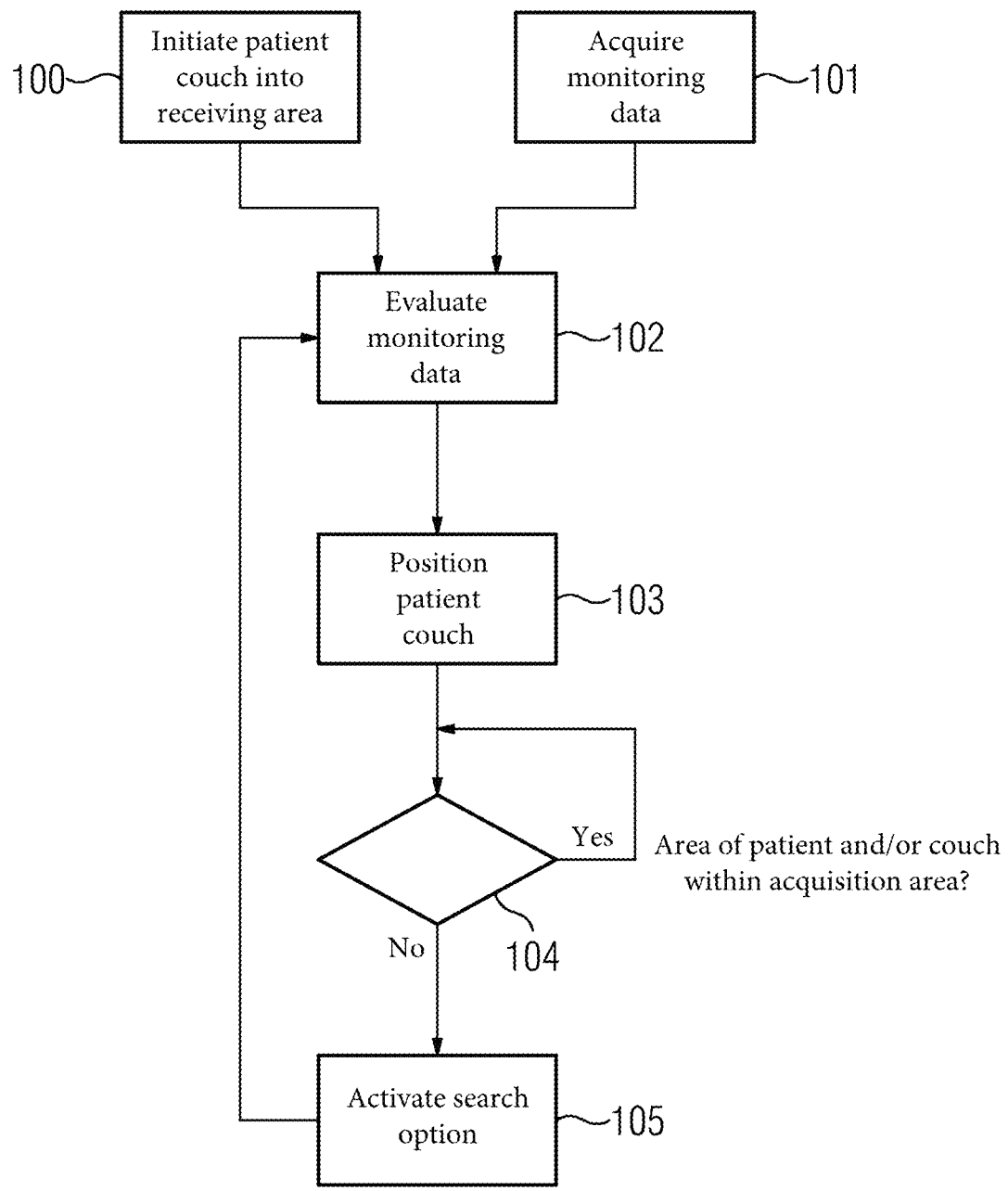

METHOD FOR POSITIONING A PATIENT COUCH IN A PATIENT RECEIVING AREA OF A MAGNETIC RESONANCE DEVICE FOR A MAGNETIC RESONANCE EXAMINATION

CROSS-REFERENCE TO RELATED APPLICATIONS

The present application claims the benefit of the filing date of German patent application no. DE 10 2019 212 863.7, filed on Aug. 27, 2019, the contents of which are incorporated herein by reference in their entirety.

TECHNICAL FIELD

The present disclosure relates to techniques for positioning a patient couch in a patient receiving area of a magnetic resonance device for a magnetic resonance examination.

BACKGROUND

Certain functions of magnetic resonance examinations on a patient require the patient to be exactly positioned within a patient receiving area, in particular within a field of view (FOV) and/or an isocenter of the magnetic resonance device. An example of such a function is motion correction, in particular camera-based motion correction, of the area of the patient to be examined. For this, the area to be examined and/or a moving area of the patient's body has to be located not only in the FOV and/or in the isocenter of a magnetic resonance device, but also in an acquisition area of sensor units, in particular in a camera acquisition area. The sensor units, for example the cameras, acquire movement data of the patient, in particular of the area of the patient to be examined, during the magnetic resonance examination on the patient and use or refer to this data for the motion correction.

However, the area to be examined and/or the moving area of the patient is frequently at least partially concealed by additional units. The result of this may be that only a limited view of the area to be examined and/or the moving area of the patient is possible and hence no acquisition of movement data by means of the sensor units, in particular the cameras, is possible. Moreover, it may also be the case that, due to a movement of the patient, the area to be examined is no longer arranged within the acquisition area of the sensor unit for the acquisition of movement data.

SUMMARY

The present disclosure is based on the object of enabling an arrangement and/or positioning of an area to be examined and/or a moving area of a patient in an acquisition area of a sensor unit during the course of a magnetic resonance examination on the patient. The object is achieved by the features as described herein, as well as the features recited in the independent and dependent claims.

The disclosure includes a method for positioning a patient couch in a patient receiving area of a magnetic resonance device for a magnetic resonance examination, wherein the method includes the following method steps:

starting an introduction of the patient couch into the patient receiving area, acquiring monitoring data within an acquisition area of at least one sensor unit by means of the at least one sensor unit during the introduction of the patient couch into the patient receiving area, evaluating the monitoring data with respect to a selected area of an examination object and/or a selected area of the patient couch, and positioning the patient couch within the patient receiving area in dependence on an acquisition of the selected area of the examination object and/or the selected area of the patient couch in the monitoring data.

The magnetic resonance device typically comprises a scanner unit with a main magnet. The main magnet is configured to generate a strong, homogeneous and constant main magnetic field, wherein the main magnet is embodied such that the strong, homogeneous and constant main magnetic field is applied in a patient receiving area, in particular in a field of view (FOV) of the magnetic resonance device. Furthermore, the scanner unit preferably includes a gradient coil unit. The gradient coil unit is configured and/or embodied to generate magnetic field gradients for spatial encoding within the patient receiving area, in particular within the FOV, during magnetic resonance imaging. The scanner unit further preferably includes a radio-frequency antenna unit, wherein the radio-frequency unit is integrated within the scanner unit. The radio-frequency antenna unit can advantageously be used to generate radio-frequency magnetic-resonance sequences and emit and/radiate them into the patient receiving area, in particular into the FOV, for excitation during the magnetic resonance examination.

The magnetic resonance device further comprises the patient receiving area, which is at least partially surrounded by the scanner unit. For example, the patient receiving area can be surrounded by the scanner unit having a cylindrical shape. The patient receiving area is configured and/or embodied to receive the patient and/or an area of the patient to be examined during a magnetic resonance examination. The patient receiving area preferably includes the FOV and/or the isocenter of the magnetic resonance device. The FOV preferably includes an acquisition area of the magnetic resonance device within which magnetic resonance data is acquired. The isocenter of the magnetic resonance device preferably includes the area and/or point within the magnetic resonance device with the most optimal and/or ideal conditions for a magnetic resonance examination. In particular, the isocenter includes the most homogenous area within the magnetic resonance device. The isocenter is preferably arranged within the patient receiving area.

Usually, a patient supporting device is arranged moveably within the patient receiving area. In particular, here a patient couch of the patient supporting device is arranged moveably in the z-direction of the scanner unit and/or in the direction of a longitudinal extension of the patient receiving area. The patient is positioned on the patient couch for the magnetic resonance examination. By means of the patient supporting device, in particular the movable patient couch, a patient, in particular an area of the patient to be examined, can be fed and/or introduced into the patient receiving area for a magnetic resonance examination and/or positioned within the patient receiving area for a magnetic resonance examination.

The introduction of the patient couch into the patient receiving area is started at the beginning of the method according to the disclosure. Here, the patient is already positioned on the patient couch for the forthcoming magnetic resonance examination. Moreover, here, the accessory units required for the forthcoming magnetic resonance examination on the patient, such as, for example, local radio-frequency antenna units and/or marking elements and/or positioning elements, etc., are already positioned on the patient and/or on the patient couch. The start of the introduction of the patient couch into the patient receiving area includes starting a movement of the patient couch in the z-direction of the scanner unit and/or in the direction of longitudinal extension of the patient receiving area into the patient receiving area. Herein, the start of the introduction of the patient couch can be started manually by a user, for example by means of a user interface of the patient supporting device and/or the magnetic resonance device comprising a start button. The introduction of the patient couch, for example the speed of the patient couch, is controlled automatically and/or autonomously by a computing unit and/or evaluation unit.

Herein, a target position can be predetermined for the introduction of the patient couch into the patient receiving area. Such a target position can, for example, be a position of an area to be examined of the examination object, in particular a patient, within the FOV and/or within the isocenter of the magnetic resonance device and/or the patient receiving area. An acquisition area and/or a viewing area of the at least one sensor unit may be at least partially directed toward the FOV and/or the isocenter of the patient receiving area and/or the magnetic resonance device.

The at least one sensor unit may be arranged within the patient receiving area. Particularly advantageously, the magnetic resonance device comprises a plurality of sensor units thus enabling redundant acquisition of the monitoring data and/or the acquisition of monitoring data from different acquisition directions. In particular, each of the sensor units of the magnetic resonance device for the acquisition of monitoring data may be arranged within the patient receiving area. The at least one sensor unit may include a camera, in particular a 3D camera and/or a HD camera. For example, the magnetic resonance device can include four cameras, e.g. four 3D cameras and/or four HD cameras. Moreover, the at least one sensor unit can also include a pilot tone sensor, which is embodied and/or configured to acquire a monitoring signal formed from an ECG signal and/or a breathing signal and/or a motion signal, and/or a breathing sensor for acquiring a monitoring signal formed from a breathing signal.

The monitoring data includes the data acquired by means of the at least one sensor unit. Thus, the monitoring data can, for example, include camera data. The acquisition of the monitoring data is preferably performed during the entire process of the introduction of the patient couch into the patient receiving area. Furthermore, it can also be provided that the acquisition of monitoring data at least partially also takes place during the magnetic resonance examination on the patient. The acquisition of the monitoring data preferably takes place automatically by means of the at least one sensor unit, wherein the acquisition of the monitoring data is controlled by the computing unit and/or the evaluation unit, in particular automatically and/or autonomously by the computing unit and/or the evaluation unit.

The evaluation of the monitoring data may take place by means of an evaluation unit and/or a computing unit. For this, the monitoring data acquired is transferred by means of a data transfer unit from the at least one sensor unit to the evaluation unit and/or to the computing unit. The data transfer unit can comprise data transfer cables for the transfer and/or exchange of data. Moreover, the data transfer unit can be embodied for wireless data transfer and/or wireless data exchange.

The evaluation unit according to the disclosure and/or the computing unit according to the disclosure includes at least one computing module and/or one processor, wherein the evaluation unit and/or the computing unit is embodied to execute the method according to the disclosure. Thus, in particular the evaluation unit and/or the computing unit is embodied to execute computer-readable instructions to execute the method according to the disclosure. In particular, the evaluation unit and/or the computing unit includes a storage unit, wherein computer-readable information is stored on the storage unit, wherein the evaluation unit and/or the computing unit is embodied to load the computer-readable information from the storage unit and execute the computer-readable information to execute the method according to the disclosure. Thus, the evaluation unit according to the disclosure and/or the computing unit according to the disclosure is embodied to execute a method for monitoring a patient during a medical imaging examination, in particular a magnetic resonance examination.

The components of the evaluation unit and/or the computing unit can be implemented in the form of software components. However, these components can also partially, in particular when particularly rapid calculations are entailed, be realized in the form of software-supported hardware components, for example FPGAs or the like. Similarly, the interfaces required, for example when only the acceptance of data from other software components is entailed, can be implemented as software interfaces. However, they can also be implemented as hardware-based interfaces that are actuated by suitable software. It is also conceivable for several of said components to be implemented as combined in the form of one single software component or software-supported hardware component.

Moreover, the evaluation of the monitoring data acquired can be based on a machine learning method, also called a deep learning method, which is based on the artificial neural network. An artificial neural network (ANN) may include a network of artificial neurons reproduced in a computer program. Herein, the artificial neural network is typically based on a network of multiple artificial neurons. The artificial neurons are typically arranged on different layers. The artificial neural network usually includes an input layer and an output layer of which the neuron output is the only visible layer of the artificial neural network. Layers between the input layer and the output layer are typically referred to as hidden layers. Typically, initially an architecture and/or topology of an artificial neural network is initiated and then trained in a training phase for a special task or in a training phase for a plurality of tasks. The training of the artificial neural network typically includes a change to a weighting of a connection between two artificial neurons of the artificial neural network. The training of the artificial neural network can also include the development of new connections between artificial neurons, the deletion of existing connections between artificial neurons, the adaptation of threshold values for the artificial neurons, the addition or deletion of artificial neurons, various combinations of these, etc.

The artificial neural network may have already been suitably trained in advance to evaluate the monitoring data acquired. Herein, the training of the artificial neural network has in particular been performed using training image datasets in which, for example in the case of the evaluation of the monitoring data with respect to a selected area of an examination object and/or a selected area of the patient couch in the monitoring data, a selected area of an examination object and/or a selected area of the patient couch is assigned. Herein, the medical training datasets are typically acquired from training people and/or training patients who are not the patient.

The selected area of the examination object, in particular of a patient, preferably includes an area of the patient to be examined. Moreover, the selected area can also include a moving area of the patient, which is in particular arranged directly next to the area to be examined. The selected area of the patient can moreover be marked for acquisition by means of the at least one sensor unit. For example, herein, the selected area of the patient can be provided with marker elements, wherein the marker elements can comprise a characteristic pattern for the identification of the selected area in the monitoring data. The selected area of the patient couch may include an area of the patient couch on which in particular the area of the patient to be examined is positioned and/or mounted.

The positioning of the patient couch within the patient receiving area may take place automatically or autonomously, wherein the positioning of the patient couch, in particular the automatic and/or autonomous positioning of the patient couch, is controlled by the evaluation unit and/or the computing unit. The positioning of the patient couch may include stopping the movement, e.g. the introductory movement, of the patient couch so that the patient couch adopts a fixed position for the forthcoming magnetic resonance examination.

An embodiment of the disclosure can advantageously enable the arrangement and/or positioning of an area to be examined and/or a moving area of a patient in an acquisition area of a sensor unit during the course of a magnetic resonance examination on the patient. Moreover, this enables the view of the at least one sensor unit of an area to be examined and/or a moving area of a patient to be maintained during a magnetic resonance examination. This enables, for example, motion correction such as camera-based motion correction, in the acquired magnetic resonance image data to take place in this way during a magnetic resonance examination. Advantageously, for motion correction such as camera-based motion correction of the acquired magnetic resonance image data during the magnetic resonance examination, further monitoring data is acquired by means of the at least one sensor unit, wherein the monitoring data acquired can be used to perform motion correction in the magnetic resonance image data. Moreover, this advantageously enables complex, time-consuming, and manual positioning of the patient couch to be dispensed with in an optimal monitoring position.

In an advantageous development of the method according to the disclosure, embodiments include the method step of positioning the patient couch including stopping a movement of the patient couch as soon as the selected area of the examination object and/or the selected area of the patient couch in the monitoring data is acquired for the first time. The first acquisition of the selected area of the examination object, e.g. the patient and/or the selected area of the patient couch advantageously enables the determination of a position of the patient couch within the patient receiving area at which the selected area of the examination object, e.g. the patient and/or the selected area of the patient couch is arranged within the acquisition area of the at least one sensor unit. Stopping the movement of the patient couch, e.g. stopping the insertion movement and/or the introductory movement of the patient couch, advantageously enables the selected area of the examination object, e.g. the patient and/or the selected area of the patient couch to be positioned and/or arranged within the acquisition area of the at least one sensor unit. Here, the stopping of the movement of the patient couch, in particular the stopping of the insertion movement and/or the introductory movement of the patient couch, may take place as soon as the selected area of the examination object, e.g. the patient and/or the selected area of the patient couch is introduced into the acquisition area of the at least one sensor unit. The stopping of the movement of the patient couch may take place automatically and/or autonomously by means of the evaluation unit and/or the computing unit.

In an advantageous development of the method according to the disclosure, embodiments include the implementation of two or more sensor units for the acquisition of monitoring data, wherein, in the method step of positioning the patient couch, the movement of the patient couch is stopped when the selected area of the examination object and/or the selected area of the patient couch in the monitoring data is acquired by at least 50% of the two or more sensor units. This advantageously enables redundant acquisition of the selected area of the examination object, e.g. the area of the patient to be examined and/or the selected area of the patient couch to be achieved. This can also provide reliable acquisition of the selected area of the examination object and/or the selected area of the patient couch during a magnetic resonance examination, for example for motion correction, e.g. camera-based motion correction, of the magnetic resonance image data acquired.

In an advantageous development of the method according to an embodiment of the disclosure, it can be provided that the method step of positioning the patient couch includes forwarding the patient couch to a predetermined (i.e. pre-determined) position of the patient couch within the patient receiving area following a first acquisition of the selected area of the examination object and/or the selected area of the patient couch in the monitoring data, wherein, during the forwarding of the patient couch, further monitoring data is acquired by means of the at least one sensor unit. Herein, the predetermined position of the patient couch can include a predetermined examination position at which the patient couch can be positioned during the course of the magnetic resonance examination. The predetermined position, e.g. the predetermined examination position, can, for example, be specified and/or established with reference to an area of the patient to be examined and/or with reference to an accessory unit arranged around the area of the patient to be examined. Herein, a position of the first acquisition of the selected area of the examination object, e.g. the patient, and/or the selected area of the patient couch in the monitoring data can be different from the predetermined position of the patient couch. Herein, the forwarding of the patient couch can include a movement of the patient couch in an insertion direction and/or in an introduction direction of the patient couch. Moreover, the forwarding of the patient couch can also include a movement of the patient couch in an exit direction, e.g. opposite to the introduction direction and/or the insertion direction, of the patient couch. This embodiment of the disclosure can advantageously enable the acquisition of a position of the patient couch at which there is a better quality of the monitoring data of the selected area of the examination object, e.g. the patient, and/or the selected area of the patient couch in the examination data. Moreover, this also enables the acquisition of a position of the patient couch at which the at least one sensor unit has a more advantageous view of the selected area of the examination object, e.g. the area of the patient to be examined and/or the selected area of the patient couch than a view on a first acquisition of the selected area of the examination object, e.g. the area of the patient to be examined and/or the selected area of the patient couch. Hence, this can also enable reliable processing of the monitoring data and a functionality associated therewith during the magnetic resonance examination.

In an advantageous development of the method according to an embodiment of the disclosure, it can be provided that the monitoring data acquired during the forwarding of the patient couch is evaluated with respect to a quality as to whether the monitoring data of the selected area of the examination object and/or the selected area of the patient couch acquired during the forwarding is of a better quality than a quality of the monitoring data on a first acquisition of the selected area of the examination object and/or the selected area of the patient couch. The quality of the monitoring data can be an image quality and/or a resolution of the monitoring data and/or a number of sensor units, which include the selected area of the examination object, e.g. the patient and/or the selected area of the patient couch, and/or a part of the selected area of the examination object acquired, e.g. the area of the patient to be examined, and/or a part of the selected area of the patient couch acquired, etc. A better quality of the monitoring data can, for example, include a better image quality, e.g. a higher resolution, in the monitoring data acquired. Moreover, a better quality of the monitoring data can also include a higher number of sensor units, which acquire the selected area of the examination object, e.g. the area of the patient to be examined and/or the selected area of the patient couch. Moreover, a better quality of the monitoring data can also include a larger part of the selected area of the examination object acquired, e.g. the area of the patient to be examined and/or a part of the selected area of the patient couch acquired, etc. This advantageously enables an optimized position to be achieved during a magnetic resonance examination for the acquisition of monitoring data for further processing of the monitoring data and/or the magnetic resonance image data in dependence on the monitoring data.

In an advantageous development of the method according to an embodiment of the disclosure, it can be provided that, if the quality of the monitoring data acquired during the forwarding is better than the quality of the monitoring data acquired on a first acquisition of the selected area of the examination object and/or the selected area of the patient couch, the position with the better quality in the monitoring data is established as the new examination position. The new examination position may include a position of the patient couch within the patient receiving area at which the patient couch is positioned during the magnetic resonance examination. This advantageously enables the achievement of an optimal position for the acquisition of monitoring data for further processing of the monitoring data and/or the magnetic resonance image data in dependence on the monitoring data.

In an advantageous development of the method according to the disclosure, it can be provided that, as soon as an acquisition of the selected area of the examination object and/or the selected area of the patient couch by means of the at least one sensor unit is interrupted during the course of the magnetic resonance examination, the patient couch executes a search movement and, during the search movement of the patient couch, monitoring data is acquired by means of the at least one sensor unit. The interruption of the acquisition of the selected area of the examination object and/or the selected area of the patient couch by means of the at least one sensor unit can be caused, for example, by a movement of the examination object, e.g. the patient, so that the selected area of the examination object, e.g. the patient, is outside the acquisition area of the at least one sensor unit and/or the selected area of the examination object, e.g. the patient, is concealed by a further unit. Particularly advantageously, the search movement of the patient couch includes a maximum movement (i.e. displacement) of the patient couch by any suitable threshold movement (e.g. ±10 cm) relative to the examination position and/or relative to the current position of the patient couch. This advantageously enables the selected area of the examination object, e.g. the area of the patient to be examined, and/or the selected area of the patient couch to be positioned once again within the acquisition area of the at least one sensor unit. Moreover, such an embodiment of the disclosure enables the continuation of a functionality associated with the monitoring data during the magnetic resonance examination, such as, for example, camera-based motion correction of the area of the patient to be examined.

Herein, it can moreover be provided that, before the start of a search movement of the patient couch is triggered, first information is output to a user, e.g. to the medical operator staff by means of a user interface of the magnetic resonance device. Moreover, it can be the case that such a search movement of the patient couch can only be started by a confirmation input by a user, e.g. the medical operating staff. The search movement of the patient couch can moreover be adapted to a current status of a magnetic resonance measurement. Herein, it is, for example, possible for the search movement only to be performed after the end of a current magnetic resonance measurement so that the patient couch and/or the area of the patient to be examined is once again positioned correctly within the patient receiving area for the following magnetic resonance measurement. Furthermore, a search movement of the patient couch can also be associated with an interruption of a current magnetic resonance measurement, wherein the current magnetic resonance measurement can be resumed once again and/or also restarted following a repositioning of the patient couch within the patient receiving area.

In an advantageous development of the method according to an embodiment of the disclosure, it can be provided that, during the execution of the search movement of the patient couch, the method step of evaluating the monitoring data with respect to a selected area of the examination object and/or the selected area of the patient couch and the method step of positioning the patient couch are executed again. Here, it is also advantageously possible for the selected area of the examination object, e.g. the area of the patient to be examined, and/or the selected area of the patient couch to be positioned once again within the acquisition area of the at least one sensor unit. Moreover, such an embodiment of the disclosure enables the continuation of a functionality associated with the monitoring data during the magnetic resonance examination, such as, for example, camera-based motion correction of the area of the patient to be examined.

In an advantageous development of the method according to an embodiment of the disclosure, it can be provided that the monitoring data includes camera data and/or data from a breathing sensor and/or data from a pilot tone sensor. This can achieve an advantageous positioning of the examination object, e.g. the patient, with respect to a breathing movement and/or a heart movement and/or an unwanted movement of the area of the patient to be examined.

Furthermore, the disclosure is based on a magnetic resonance device with a scanner unit, a patient receiving area which is at least partially surrounded by the scanner unit, a patient couch that can be moved within the patient receiving area, at least one sensor unit, and a computing unit, wherein the magnetic resonance device is configured to execute the method for positioning the patient couch in the patient receiving area for a magnetic resonance examination.

A magnetic resonance device embodied in this way can advantageously enable an arrangement and/or a positioning of an area to be examined and/or a moving area of a patient in an acquisition area of a sensor unit during the course of a magnetic resonance examination on the patient. Moreover, this enables a view of the at least one sensor unit of an area to be examined and/or a moving area of a patient to be maintained during a magnetic resonance examination. This, for example, enables motion correction, e.g. camera-based motion correction, to take place in the magnetic resonance image data acquired during a magnetic resonance examination. Advantageously, for motion correction, e.g. camera-based motion correction, of the magnetic resonance image data acquired, during the magnetic resonance examination further monitoring data is acquired by means of the at least one sensor unit, wherein the motion correction in the magnetic resonance image data can be performed with reference to the monitoring data acquired. Moreover, this also advantageously enables complex, time-consuming, and manual positioning of the patient couch to be dispensed with in an optimal monitoring position.

The advantages of the magnetic resonance device embodiments according to the disclosure substantially correspond to the advantages of the method embodiments according to the disclosure for positioning the patient couch in the patient receiving area for a magnetic resonance examination and the embodiments of the computer-program that may perform the method embodiments when executed by one or more processors, as explained in detail herein. Features, advantages or alternative embodiments mentioned herein can also be transferred to the other embodiments, and vice versa.

In an advantageous development of the magnetic resonance device according to an embodiment of the disclosure, it can be provided that the at least one sensor unit has an acquisition area, wherein the acquisition area comprises a predetermined acquisition area within the patient receiving area. Particularly advantageously, the predetermined acquisition area is directed toward the FOV and/or the isocenter of the patient receiving area and/or the magnetic resonance device, thus enabling an advantageous acquisition of a movement of an area to be examined during the magnetic resonance examination to be achieved.

In an advantageous development of the magnetic resonance device according to an embodiment of the disclosure it can be provided that the at least one sensor unit includes a camera and/or a breathing sensor and/or a pilot tone sensor. The camera may include a 3D camera and/or a HD camera for the acquisition of 3D-monitoring data and/or for the acquisition of HD monitoring data. The breathing sensor can advantageously acquire a breathing movement of the patient. The pilot tone sensor can advantageously acquire a breathing movement and/or a heart movement of the patient. The pilot tone sensor can acquire a monitoring signal, wherein the monitoring signal is independent of a magnetic resonance signal and/or an excitation signal and/or outside a magnetic resonance signal and/or excitation signal. Herein, the pilot tone signal can be phase-modulated and/or amplitude-modulated.

Furthermore, the disclosure is based on a computer program product, which includes a program and can be loaded directly into a memory (e.g. a non-transitory computer-readable media) of a programmable computing unit, with program means for executing a method for positioning a patient couch in a patient receiving area of a magnetic resonance device for a magnetic resonance examination when the program is executed in the computing unit. Herein, the computer program may require program means, for example libraries and auxiliary functions to implement the corresponding embodiments of the method. Herein, the computer program can include software with a source code which still has to be compiled and linked or only has to be interpreted or an executable software code that only needs to be loaded into a corresponding computing unit (e.g. a computing unit associated with the magnetic resonance device as discussed herein) for execution.

The computer program product according to the disclosure can be loaded directly into a memory of a programmable computing unit and/or control unit and has program code means for executing a method according to the disclosure when the computer program product is executed in the computing unit and/or control unit. The computer program product can be a computer program or include a computer program. This enables the method according to the disclosure to be executed quickly, identically repeatably, and robustly. The computer program product is configured such that it can execute the method steps according to the disclosure by means of the computing unit and/or control unit, which may form part of a magnetic resonance device and thus facilitate the method to be performed by the magnetic resonance device. Herein, the computing unit and/or control unit fulfill the requisite conditions such as, for example, having an appropriate random-access memory, an appropriate graphics card or an appropriate logic unit so that the respective method steps can be executed efficiently. The computer program product is, for example, stored on a computer-readable medium or held on a network or server from where it can be loaded into the processor of a local computing unit and/or control unit, which is directly connected to the magnetic resonance device or can be embodied as part of the magnetic resonance device. Further, control information of the computer program product can be stored on an electronically readable data carrier. The control information of the electronically readable data carrier can be embodied to execute the method according to the disclosure when the data carrier is used in a computing unit and/or control unit. For example, the computer program product can also represent the electronically readable data carrier. Examples of electronically readable data carriers are DVDs, magnetic tapes, hard disks or USB sticks on which electronically readable control information, e.g. software (see above), is stored. When this control information (software) is read from the data carrier and stored in a control system and/or computing unit and/or control unit, each of the embodiments of the above-described method can be performed. For example, the disclosure can also be based on said computer-readable medium and/or said electronically readable data carrier.

Furthermore, the disclosure is based on a computer-readable data carrier, which includes a program provided to execute a method for positioning a patient couch in a patient receiving area of a magnetic resonance device for a magnetic resonance examination.

BRIEF DESCRIPTION OF THE DRAWINGS/FIGURES

Further advantages, features and details of the disclosure will emerge from the exemplary embodiment described in the following and with reference to the drawings.

FIG. 1 is a schematic depiction of a magnetic resonance device, in accordance with one or more embodiments of the present disclosure; and FIG. 2 is a method for positioning a patient couch in a patient receiving area of a magnetic resonance device for a magnetic resonance examination, in accordance with one or more embodiments of the present disclosure.

DETAILED DESCRIPTION

FIG. 1 is a schematic representation of magnetic resonance device 10. The magnetic resonance device 10 includes a scanner unit 11 formed by a magnet unit. Moreover, the magnetic resonance device 10 comprises a patient receiving area 12 for receiving a patient 13. In the present exemplary embodiment, the patient receiving area 12 has a cylindrical shape and is cylindrically surrounded by the scanner unit 11, in particular the magnet unit, in a circumferential direction. However, a different embodiments of the patient receiving area 12 are conceivable.

The patient 13 can be pushed and/or moved into the patient receiving area 12 by means of a patient supporting device 14 of the magnetic resonance device 10. For this, the patient supporting device 14 comprises a movable patient couch 15 within the patient receiving area 12. Here, in particular the patient couch 15 is mounted moveably in the direction of a longitudinal extension 16 and/or a longitudinal direction of the patient receiving area 12 and/or in the z-direction of the patient receiving area 12. To control the patient couch 15, in particular to control a movement of the patient couch 15, the magnetic resonance device 10 comprises a computing unit 17, which may include one or more processors and be alternatively referred to herein as a computer 17 or computing circuitry 17. For this, the computing unit 17 comprises the necessary control software and/or control programs, which are stored in a memory of the computing unit 17 that is not depicted in further detail.

The scanner unit 11, in particular the magnet unit, comprises a superconducting main magnet 18 for generating a strong and in particular constant main magnetic field 19. The scanner unit 11, in particular the magnet unit, further comprises a gradient coil unit 20 for generating magnetic field gradients that are used for spatial encoding during imaging. The gradient coil unit 20 is controlled by means of a gradient control unit 21 of the magnetic resonance device 10. The scanner unit 11, in particular the magnet unit, further includes a radio-frequency antenna unit 22 for exciting a polarization which is established in the main magnetic field 19 generated by the main magnet 18. The radio-frequency antenna unit 22 is controlled by a radio-frequency antenna control unit 23 of the magnetic resonance device 10 and radiates radio-frequency magnetic resonance sequences into the patient receiving area 12 of the magnetic resonance device 10.

To control the main magnet 18, the gradient control unit 21 and the radio-frequency antenna control unit 23, the magnetic resonance device 10 comprises a system control unit 24, which may include one or more processors and be alternatively referred to herein as a control computer 24 or control computing circuitry 24. The system control unit 24 centrally controls the magnetic resonance device, such as, for example, the performance of a predetermined imaging gradient echo sequence. For this, the system control unit 24 includes control software and/or control programs, which are stored in a storage unit of the system control unit 24 which is not depicted in any further detail. The control software and/or control programs are executed by means of a processor of the system control unit 24 that is not depicted in any further detail. Moreover, the system control unit 24 includes an evaluation unit that is not depicted in any further detail for the evaluation of medical image data acquired during the magnetic resonance examination. The evaluation unit may also include one or more processors and be alternatively referred to herein as an evaluation computer or evaluation computing circuitry 24

To control the patient supporting device 14, in particular to control a movement of the patient couch 15, in the present exemplary embodiment, the computing unit 17 is embodied separately from the system control unit 24. Data exchange between the computing unit 17 and the system control unit 24 takes place via a data transfer unit. Moreover, to control the patient supporting device 14, in particular to control the movement of the patient couch 15, the computing unit 17 can also be integrated within the system control unit 24.

Furthermore, the magnetic resonance device 10 includes a user interface 25 connected to the system control unit 24. Control information such as, for example, imaging parameters, and reconstructed magnetic resonance images can be displayed to medical operating staff on a display unit 26, for example on at least one monitor, of the user interface 25. The user interface 25 further comprises an input unit 27, by means of which information and/or parameters can be input by the medical operating staff during a measuring process.

The magnetic resonance device 10 further includes at least one sensor unit 28 (e.g. a sensor system or one or more individual sensor components) for acquiring monitoring data. In the present exemplary embodiment, the magnetic resonance device 10 includes four sensor units 28. The individual sensor units 28 are in each case formed by a camera, e.g. a 3D camera and/or an HD camera. Moreover, the individual sensor units 28, e.g. the individual cameras, are arranged within the patient receiving area 12. However, the arrangement of the sensor units 28, in particular the cameras, is not restricted to the patient receiving area 12 of the magnetic resonance device 10, and the individual sensor units 18 can also be arranged outside the patient receiving area.

The individual sensor units 28, e.g. the individual cameras in each case comprise an acquisition area 29, which is directed at a FOV and/or an isocenter of the patient receiving area 12 and/or the magnetic resonance device 10. Herein, the individual acquisition areas 29 of the respective sensor unit 28, in particular the respective camera, include predetermined acquisition areas 29. The individual sensor units 28, e.g. the individual cameras, acquire monitoring data that includes camera data.

In an alternative embodiment of the disclosure, the magnetic resonance device 10 can also comprise more than four sensor units 28 or fewer than four sensor units 28. Moreover, the individual sensor units 28 can also include a breathing sensor and/or a pilot tone sensor and/or further sensors that appear advisable to the person skilled in the art. Herein, a breathing sensor and/or a pilot tone sensor can also acquire monitoring data.

FIG. 2 depicts the sequence of a method according to the disclosure for positioning the patient couch 15 in the patient receiving area 12 of the magnetic resonance device 10 for a magnetic resonance examination. The method for positioning the patient couch 15 in the patient receiving area 12 of the magnetic resonance device 10 is executed by means of the computing unit 17 to control the patient supporting device 14, in particular to control the movement of the patient couch 15. Here, individual method steps of the method are executed automatically and/or autonomously by means of the computing unit 17. For this, the computing unit 17 comprises software and/or computer programs, in particular control software and/or control programs to control the movement of the patient couch 15, which are stored in a storage unit of the computing unit 17 that is not depicted in any further detail. Moreover, the storage unit can also be arranged outside the computing unit 17 and herein included in the magnetic resonance device 10. Furthermore, the storage unit can also include a storage unit that is external to the magnetic resonance device 10, such as, for example, a separate data carrier. To execute the method for positioning the patient couch 15 in the patient receiving area 12 of the magnetic resonance device 10, the software and/or computer programs are executed by a processor of the computing unit 17.

Before the method according to the disclosure for positioning the patient couch 15 in the patient receiving area 12 of the magnetic resonance device 10 is started, the patient 13 is preferably already positioned on the patient couch 15 for the forthcoming magnetic resonance examination. Moreover, here, all the accessory units required for the forthcoming magnetic resonance examination, such as, for example, local radio-frequency antenna units and/or positioning and/or support cushions and/or communication elements, such as, for example, headphones, are also already positioned on the patient couch 15 and/or on the patient 13.

In a first method step 100 of the method according to the disclosure for positioning the patient couch 15 in the patient receiving area 12 of the magnetic resonance device 10, the introduction of the patient couch 15 into the patient receiving area 12 is started. Preferably, the start of the introduction of the patient couch 15 into the patient receiving area 12 is initiated by a user, in particular medical operating staff, in that, for example, the start button is pressed by the user, in particular the medical operating staff. Here, the start button can be arranged directly on the patient couch 15. Moreover, the start button can also be arranged on a touch display arranged on the scanner unit 11 that is not depicted in any further detail. The execution of the start of the introduction of the patient couch 15 into the patient receiving area 12 then takes place automatically and/or autonomously by means of the computing unit 17. For example, here the computing unit 17 can set the speed of the patient couch 15 and/or introduction route, etc. Here, an introductory movement of the patient couch 15 into the patient receiving area 12 takes place in the z-direction of the magnetic resonance device 10 and/or in the direction of the longitudinal extension 16 of the patient receiving area 12.

Simultaneously with the start of the introduction of the patient couch 15 into the patient receiving area 12, in a second method step 101, monitoring data is acquired within an acquisition area 29 of the at least one sensor unit 28 by means of the at least one sensor unit 28. For instance, monitoring data from as camera may be acquired by means of the four cameras in the second method step 101.

In a third method step 102, the monitoring data is evaluated, wherein the evaluation of the monitoring data takes place with respect to a selected area (e.g. an identified area) of the examination object, in particular the patient 13, and/or with respect to a selected area (e.g. an identified area) of the patient couch 15. The selected area of the patient 13 may include the area of the patient 13 to be examined. The evaluation of the monitoring data takes place by means of the computing unit 17, in particular automatically and/or autonomously by means of the computing unit 17.

In a subsequent fourth method step 103, the patient couch 15 is positioned in dependence on an acquisition of the selected (e.g. identified) area of the examination object, e.g. based upon the area of the patient to be examined 13, and/or the selected (e.g. identified) area of the patient couch 15 in the monitoring data. Herein, the positioning of the patient couch 15 includes stopping a movement of the patient couch 15, wherein the stopping of the movement of the patient couch 15 is controlled by the computing unit 17, e.g. automatically and/or autonomously. The stopping of the movement of the patient couch 15 may occur as soon as the selected area of the examination object, e.g. the area of the patient to be examined 13, and/or the selected area of the patient couch 15 is acquired for the first time in the monitoring data. In the present exemplary embodiment, the movement of the patient couch 15 is stopped when the selected area of the examination object, e.g. the area of the patient to be examined 13, and/or the selected area of the patient couch 15 in the monitoring data is acquired by at least 50% of the two or more sensor units 28. For example, the movement of the patient couch 15 may be stopped when the selected area of the examination object, e.g. the area of the patient to be examined 13, and/or the selected area of the patient couch 15 in the monitoring data is acquired by at least two of the four cameras.

Alternatively to immediately stopping the movement of the patient couch 15 on the first acquisition of the selected area of the examination object, e.g. the area of the patient to be examined 13 and/or the selected area of the patient couch 15, it can also be provided in the fourth method step 103 of the positioning that the patient couch 15 is forwarded to (e.g. moved to) a predetermined position within the patient receiving area 12. Here, after the first acquisition of the selected area of the examination object, e.g. the area of the patient to be examined 13 and/or the selected area of the patient couch 15, the patient couch 15 is forwarded (e.g. moved) to the predetermined position within the patient receiving area 12, wherein, during the forwarding of the patient couch 15, further monitoring data is acquired by means of the at least one sensor unit 28, e.g. by means of the four cameras.

The monitoring data acquired during the forwarding of the patient couch 15 to the predetermined position within the patient receiving area 12 is evaluated by the computing unit 17, e.g. automatically and/or autonomously by the computing unit 17, with respect to quality. Herein, the quality of the monitoring data of the selected area of the examination object, e.g. the area of the patient to be examined 13 and/or the selected area of the patient couch 15 acquired during the forwarding is determined and or ascertained, e.g. automatically and/or autonomously, by the computing unit 17. Moreover, the computing unit 17 automatically or autonomously compares the quality of the monitoring data acquired during the forwarding with a quality of the monitoring data acquired on a first acquisition of the selected area of the examination object, e.g. the area of the patient 13 to be examined and/or the selected area of the patient couch 15, and ascertains whether the monitoring data acquired during the forwarding of the selected area of the examination object, e.g. the area of the patient to be examined 13 and/or the selected area of the patient couch 15 is of a better quality than a quality of the monitoring data on the first acquisition of the selected area of the examination object, e.g. the area of the patient 13 to be examined and/or the selected area of the patient couch 15.

The quality of the monitoring data can include an image quality and/or a resolution of the monitoring data and/or a number of sensor units 28, which acquire the selected area of the examination object, e.g. the area of the patient to be examined 13 and/or the selected area of the patient couch 15, and/or a part of the selected area of the examination object acquired, e.g. the area of the patient to be examined 13, and/or a part of the selected area of the patient couch acquired 15, etc. A better quality of the monitoring data can, for example, be a better image quality, in particular a higher resolution, in the monitoring data acquired. Moreover, a better quality of the monitoring data can also include a higher number of sensor units 28, which acquire the selected area of the examination object, e.g. the area of the patient to be examined 13 and/or the selected area of the patient couch 15. Moreover, a better quality of the monitoring data can also include a greater part of the selected area of the examination object acquired, in particular the area of the patient to be examined 13 and/or a part of the selected area of the patient couch acquired 15, etc.

If the quality of the monitoring data acquired during the movement is better than the quality of the monitoring data acquired on the first acquisition of the selected area of the examination object, e.g. the area of the patient to be examined 13 and/or the selected area of the patient couch 15, a position at which the better quality of monitoring data acquired during the forwarding was acquired is established, e.g. automatically and/or autonomously, by the computing unit 17 as the new examination position. If the quality of the monitoring data acquired during the forwarding is equal to or worse than the quality of the monitoring data acquired on the first acquisition of the selected area of the examination object, e.g. the area of the patient to be examined 13 and/or the selected area of the patient couch 15, the previously set examination position and/or the predetermined examination position is retained.

When the fourth method step 103 of the positioning of the patient couch 15 within the patient receiving area 12 has been performed, further monitoring data is acquired by means of the at least one sensor unit 28, e.g. by means of the four cameras, in a fifth method step 104. Herein, a check is performed as to whether the selected area of the examination object, e.g. the area of the patient to be examined 13 and/or the selected area of the patient couch 15 is further within the acquisition area 29 of the least one sensor unit 28, e.g. within the acquisition areas 29 of the four cameras, and is acquired by the at least one sensor unit 28. In the present case, the computing unit 17 automatically and/or autonomously checks whether the selected area of the examination object, e.g. the area of the patient to be examined 17 and/or the selected area of the patient couch 15 in the monitoring data is acquired by at least 50% of the four cameras, e.g. two of the four cameras.

If the check in the fifth method step reveals that the selected area of the examination object, e.g. the area of the patient to be examined 13 and/or the selected area of the patient couch 15 in the monitoring data is acquired by two or more of the cameras, the previously set examination position and/or the predetermined examination position is maintained and the cameras further acquire monitoring data of the selected area of the examination object, e.g. the area of the patient to be examined 13 and/or the selected area of the patient couch 15.

However, if the check reveals that the selected area of the examination object, e.g. the area of the patient to be examined 13 and/or the selected area of the patient couch 15 in the monitoring data is acquired by fewer than two of the four cameras during the course of the magnetic resonance examination on the patient 15, a search option is activated at least partially automatically and/or autonomously by the computing unit 17 in a sixth method step 105. Herein, it can be provided that initially output information for the user, e.g. the medical operating staff, is generated by the computing unit 17 and output to the user, e.g. the medical operating staff, by means of the display unit 25 of the user interface 25. Moreover, it can be the case that such a search movement of the patient couch 15 can only be started automatically and/or autonomously by the computing unit 17 by a confirmation input by a user, e.g. the medical operating staff. For instance, the search option may be activated by the computing unit 17 as soon as there is an interruption in the acquisition of the selected area of the examination object, e.g. the area of the patient 13 to be examined, and/or the selected area of the patient couch 15 by at least three of the four cameras during the course of the magnetic resonance examination on the patient 13.

Herein, this search option includes a search movement and a repositioning of the patient couch 15. The search movement of the patient couch 15 is controlled automatically and/or autonomously by the computing unit 17. The search movement of the patient couch 15 includes a maximum movement of the patient couch 15 of any suitable threshold value depending upon the particular implementation, which may include ±10 cm in the z-direction of the magnetic resonance device 10 and/or in the longitudinal extension 16 of the patient receiving area 12, for instance. Herein, during the execution of the search movement of the patient couch 15, the third method step 102 of the evaluation of the monitoring data with respect to the selected area of the examination object and/or the selected area of the patient couch 15 and the fourth method step 103 of the positioning of the patient couch 15 are executed once again.

The search movement of the patient couch 15 and the repositioning of the patient couch 15 within the patient receiving area 12 can moreover be adapted to a current status of a magnetic resonance measurement and/or a magnetic resonance examination. Herein, the search movement of the patient couch 15 and/or the repositioning of the patient couch 15 within the patient receiving area 12 may, for example, only be performed after the end of a current magnetic resonance measurement so that the patient couch 15 and/or the area of the patient 13 to be examined are once again positioned correctly within the patient receiving area 12 for the subsequent magnetic resonance measurement. Furthermore, a search movement of the patient couch 15 can be associated with an interruption in a current magnetic resonance measurement, wherein the current magnetic resonance measurement can be resumed once again and/or also restarted after a repositioning of the patient couch 15 within the patient receiving area 12.

The magnetic resonance device 10 depicted herein may include a greater number, a lesser number, or alternate components that are generally included in magnetic resonance devices 10. Moreover, the general mode of operation of a magnetic resonance device 10 is known to the person skilled in the art so that additional details with respect to its overall operation are not provided for purposes of brevity.

Although the disclosure has been illustrated and described in greater detail by the preferred exemplary embodiments, the disclosure is not restricted by the disclosed examples and other variations can be derived by a person skilled in the art without departing from the scope of protection of the disclosure. Further, the above descriptions are preferred embodiments of the present disclosure but not intended to limit the present disclosure, and any modifications, equivalent replacements, improvements, etc. made within the spirit and principle of the present disclosure should be included within the scope of protection of the present disclosure.

The various functional blocks, apparatuses, modules, units, components of physical or functional units, etc., as shown in the drawings and described herein may be implemented unless otherwise noted via any suitable number and type of computer processors, hardware components, the execution of software algorithms, or combinations thereof, and thus may alternatively be referred to as a "unit," "system," "circuitry," or "device."

What is claimed is:

1. A method for positioning a patient couch in a patient receiving area of a magnetic resonance device for a magnetic resonance examination, comprising:
    initiating, via one or more processors, movement of the patient couch into the patient receiving area;
    acquiring, via at least one sensor associated with an acquisition area within the patient receiving area, monitoring data during the movement of the patient couch into the patient receiving area;
    evaluating, via the one or more processors, the monitoring data to identify an area of an examination object that comprises (i) an area of a patient and/or (ii) an area of the patient couch; and
    positioning, via the one or more processors, the patient couch within the patient receiving area based upon the identified area of the examination object by:
        iteratively determining, during the movement of the patient couch into the patient receiving area, whether the identified area of the examination object remains within the acquisition area of the at least one sensor;
        while the identified area of the examination object remains within the acquisition area of the at least one sensor, advancing the patient couch towards a predetermined examination position; and
        when the identified area of the examination object is no longer within the acquisition area of the at least one sensor, (i) temporarily stopping the advancing of the patient couch towards the predetermined examination position, (ii) moving the patient couch in accordance with a predetermined search movement profile, and (iii) repeating the act of evaluating the monitoring data to re-identify the area of the examination object.

2. The method as claimed in claim 1, wherein the act of positioning the patient couch includes stopping movement of the patient couch when (i) the identified area of the patient and/or (ii) the identified area of the patient couch is acquired for a first time in the monitoring data.

3. The method as claimed in claim 1, wherein:
    the at least one sensor is from among a plurality of sensors;
    acquiring the monitoring data comprises acquiring, via the plurality of sensors, the monitoring data; and
    positioning the patient couch comprises stopping movement of the patient couch when (i) the identified area of the patient and/or (ii) the identified area of the patient couch is acquired by at least 50% of the plurality of sensors.

4. The method as claimed in claim 1, further comprising:
    moving the patient couch to the predetermined examination position subsequent to (i) the identified area of the patient and/or (ii) the area of the patient couch being acquired for a first time in the monitoring data as part of a first acquisition; and
    acquiring, during the movement of the patient couch to the predetermined examination position, additional monitoring data of (i) the identified area of the patient and/or (ii) the identified area of the patient couch.

5. The method as claimed in claim 4, further comprising:
    evaluating the additional monitoring data acquired during the movement of the patient couch to determine whether the additional monitoring data is of a better quality than the monitoring data acquired as part of the first acquisition.

6. The method as claimed in claim 5,
    wherein, when the quality of the additional monitoring data is better than the quality of the monitoring data acquired as part of the first acquisition, updating the position of (i) the identified area of the patient and/or (ii) the identified area of the patient couch as a new examination position.

7. The method as claimed in claim, 1
    wherein the predetermined search movement profile of the patient couch includes a displacement of the patient couch of no more than ±10 cm from a patient couch position prior to the predetermined search movement profile being executed.

8. The method as claimed in claim 1, wherein the at least one sensor comprises one or more of a camera, a breathing sensor, or a pilot tone sensor, and
    wherein the monitoring data includes camera data generated via the camera, data generated via the breathing sensor, or data generated via the pilot tone sensor.

9. The method as claimed in claim 1, wherein the act of moving the patient couch in accordance with the predetermined search movement profile and repeating the act of evaluating the monitoring data to re-identify the area of the examination object is performed in response to a current status of the magnetic resonance examination.

10. The method as claimed in claim 9, wherein the current status of the magnetic resonance examination comprises an interruption in a magnetic resonance measurement.

11. The method as claimed in claim 1, wherein the at least one sensor compromises a plurality of sensors, and
    wherein the identified area of the examination object is no longer within the acquisition area of the at least one sensor when the identified area of the examination object is no longer within a respective acquisition area of less than half of the plurality of sensors.

12. The method as claimed in claim 1, wherein the patient receiving area comprises a cylindrical shape, which is cylindrically surrounded by a magnet identified with the magnetic resonance device in a circumferential direction, and
    wherein the movement of the patient couch into the patient receiving area is in a direction of longitudinal extension of the patient receiving area and of the magnet of the magnetic resonance device.

13. The method as claimed in claim 12, wherein the direction of longitudinal extension of the patient receiving area is perpendicular to a direction identified with a thickness of the patient couch.

14. The method as claimed in claim 1, wherein the movement of the patient couch into the patient receiving area comprises a different motion trajectory than the predetermined search movement profile.

15. A magnetic resonance device, comprising:
    a scanner unit;
    a patient receiving area that is at least partially surrounded by the scanner unit;
    a patient couch configured to be moved within the patient receiving area;
    at least one sensor associated with an acquisition area within the patient receiving area; and
    one or more processors configured to:
        initiate movement of the patient couch into the patient receiving area for a magnetic resonance examination;

acquire, via the at least one sensor, monitoring data from the acquisition area during the movement of the patient couch into the patient receiving area;

evaluate the monitoring data to identify an area of an examination object that comprises (i) an area of an examination object and/or (ii) an area of the patient couch; and position the patient couch within the patient receiving area based upon the identified area of the examination object by:

iteratively determining, during the movement of the patient couch into the patient receiving area, whether the identified area of the examination object remains within the acquisition area of the at least one sensor;

while the identified area of the examination object remains within the acquisition area of the at least one sensor, advancing the patient couch towards a predetermined examination position; and when the identified area of the examination object is no longer within the acquisition area of the at least one sensor, (i) temporarily stopping the advancing of the patient couch towards the predetermined examination position, (ii) moving the patient couch in accordance with a predetermined search movement profile, and (iii) repeating the evaluating of the monitoring data to re-identify the area of the examination object.

16. The magnetic resonance device as claimed in claim 15, wherein the acquisition area associated with the at least one sensor includes a predetermined acquisition area within the patient receiving area.

17. The magnetic resonance device as claimed in claim 15, wherein the at least one sensor comprises one or more of a camera, a breathing sensor, or a pilot tone sensor.

18. A non-transitory computer-readable media having instructions stored thereon that, when executed by one or more processors of a magnetic resonance device, cause the magnetic resonance device to:

initiate movement of a patient couch into a patient receiving area of the magnetic resonance device for a magnetic resonance examination;

acquire, via at least one sensor associated with an acquisition area within the patient receiving area, monitoring data during the movement of the patient couch into the patient receiving area;

evaluate the monitoring data to identify an area of an examination object that comprises (i) an area of an examination object and/or (ii) an area of the patient couch; and position the patient couch within the patient receiving area based upon the identified area of the examination object by:

iteratively determining, during the movement of the patient couch into the patient receiving area, whether the identified area of the examination object remains within the acquisition area of the at least one sensor;

while the identified area of the examination object remains within the acquisition area of the at least one sensor, advancing the patient couch towards a predetermined examination position; and when the identified area of the examination object is no longer within the acquisition area of the at least one sensor, (i) temporarily stopping the advancing of the patient couch towards the predetermined examination position, (ii) moving the patient couch in accordance with a predetermined search movement profile, and (iii) repeating the evaluating of the monitoring data to re-identify the area of the examination object.

* * * * *